(12) United States Patent
Hecht et al.

(10) Patent No.: US 7,816,024 B2
(45) Date of Patent: Oct. 19, 2010

(54) POWER GENERATION DEVICE UTILIZING LIVING PLANT NUTRIENTS

(75) Inventors: Mathias Hecht, Tucson, AZ (US); Matt Wallen, Tucson, AZ (US)

(73) Assignee: Advanced Ceramics Manufacturing, LLC, Tucson, AZ (US)

( * ) Notice: Subject to any disclaimer, the term of this patent is extended or adjusted under 35 U.S.C. 154(b) by 618 days.

(21) Appl. No.: 11/774,974

(22) Filed: Jul. 9, 2007

(65) Prior Publication Data

US 2009/0017336 A1 Jan. 15, 2009

(51) Int. Cl.
*H01M 8/16* (2006.01)
(52) U.S. Cl. ......................................................... 429/2
(58) Field of Classification Search ........................ None
See application file for complete search history.

(56) References Cited

U.S. PATENT DOCUMENTS

| | | | |
|---|---|---|---|
| 5,464,539 A * | 11/1995 | Ueno et al. ................. 210/603 |
| 6,311,429 B1 * | 11/2001 | Wolfe ......................... 47/57.5 |
| 6,500,571 B2 * | 12/2002 | Liberatore et al. ............. 429/2 |
| 6,686,075 B2 * | 2/2004 | Gieshoff et al. ................ 429/2 |
| 6,887,692 B2 * | 5/2005 | Paterek ....................... 435/168 |
| 6,984,305 B2 * | 1/2006 | McAlister ................... 205/637 |
| 7,033,822 B2 * | 4/2006 | Maston ................... 435/290.1 |
| 7,160,637 B2 * | 1/2007 | Chiao et al. ..................... 429/2 |

* cited by examiner

*Primary Examiner*—Herbert J. Lilling
(74) *Attorney, Agent, or Firm*—Banner & Witcoff, Ltd.

(57) ABSTRACT

A power generation device includes a gas producing section for the extraction and utilization of living plant nutrients to produce a hydrogen containing gas and a hydrogen utilizing section coupled to the gas producing section, wherein the hydrogen content of the gas is used to generate electrical energy. The gas producing section includes a housing adapted to be connected to a living plant and placed in communication with a nutrient containing region of the plant, a chamber within the housing containing a bacterium capable of converting the plant nutrients into the hydrogen containing gas, and a pathway adapted to bring the plant nutrients into contact with the bacterium.

5 Claims, 3 Drawing Sheets

POWER GENERATION DEVICE UTILIZING LIVING PLANT NUTRIENTS

TECHNICAL FIELD

The invention relates to a new electrical power supply, and, more specifically, to a device that converts nutrients produced in living plants into a gas containing hydrogen via bacteria.

BACKGROUND AND PRIOR ART

Wireless and portable electronic devices, sensors, and cameras need independent power supplies to enable operation in areas where the electrical grid is not easily accessible. Currently, batteries are used to power the majority of the devices, which are finite energy sources that are susceptible to environmental conditions such as high or low temperatures. The shortcomings of these energy sources limit the operating time of the devices. As a result, the batteries have to be frequently recharged or replaced to extend the operating time of the devices. Recharging typically needs access to the grid and to power conversion electronics. The alternative method of battery replacement is a significant cost factor and raises environmental concerns.

The most viable alternative to batteries is power harvesting from the environment. Typically, wind or solar energy are used. However, these power harvesting devices have to be rather large and will not work when there is no light (at night) or wind. Other alternatives such as vibration or thermal energy harvesting are limited to very small application areas where vibrations or thermal gradients are present. An alternative would be to utilize the oxygen in air to oxidize fuel compounds produced by ubiquitous plants. These fuels consist of carbohydrates that have been produced via photosynthetic or metabolic pathways.

The utilization of such fuels to produce electrical power has been described before. Fuel cells have been constructed that use the nutrients directly or with the help of electron transfer mediators. The problems with such fuel cells are that the nutrients are in direct contact with either the catalysts or the mediator compounds, which results in catalyst or mediator deactivation/poising. As a result, the operating time of such devices is very limited. For example, U.S. Pat. No. 7,160,637 discloses the utilization of sugars such as glucose to power a direct conversion microbial fuel cell. However, the total performance duration displayed is less than 5 hours. Such a fuel cell has also been disclosed in U.S. Pat. No. 6,500,571, where redox enzymes have been used as electron transfer mediators.

Organic waste has also been used to produce hydrogen containing gases. For example, in U.S. Pat. No. 5,464,539, waste streams containing cellulose and sugar complexes are utilized as a feed stream for micro-organisms to produce mixtures of hydrogen and carbon dioxide. Another process described in U.S. Pat. No. 6,984,305 converts solid waste in an anaerobic reaction with the help of microorganisms and an applied voltage into a gas containing hydrogen. Similarly, U.S. Pat. No. 7,033,822 discloses a process to convert organic waste materials into high purity hydrogen by adding a gas purification device to separate the gas mixture produced by an anaerobic decomposition reaction. In addition, a method for hydrogen production from biodegradable feedstock using a two-stage anaerobic bioreactor has been described in U.S. Pat. No. 6,887,692. Light and photosynthetic bacteria are used in this process to produce the gas.

An exemplary embodiment of the present invention utilizes nutrient containing liquids from living plants as the fuel material. The device interfaces with the plant for extended periods and does not significantly impede natural functions, which keeps the plant alive. Related methods to form such an interface are techniques used to distribute nutrients and medicine to living plants. For example, in U.S. Pat. No. 6,311,429, a tree implant device is disclosed that supplies medication into the phloem layer for distribution within trees. The device makes use of the sap pressure within trees to squeeze medication from the device over an extended period of time. This naturally occurring sap pressure can be utilized as the fuel delivery mechanism in the present invention.

The tree implant device of the current invention introduces a new class of energy harvesting device in which energy in the form of plant nutrients is utilized for the production of hydrogen. The invention solves the problems discussed above and provides advantages that are not possible with other power harvesting methods. A discussion of the features and advantages of the present invention is deferred to the following description.

SUMMARY OF THE INVENTION

Aspects of the invention relate generally to a power generation device that includes a gas producing section for the extraction and utilization of living plant nutrients to produce a hydrogen containing gas and a hydrogen utilizing section coupled to the gas producing section. The hydrogen utilization section generates electrical energy using the produced gas. The gas producing device includes a housing adapted to be connected to a living plant and placed in communication with a nutrient containing region of the plant, a chamber within the housing containing a bacterium capable of converting the plant nutrients into a hydrogen containing gas, and a pathway adapted to bring the plant nutrients into contact with the bacterium.

Other aspects of the invention relate to a method for producing usable electricity for an extended period of time, including several steps. A gas producing device is provided, having a chamber containing a bacterium capable of converting plant nutrients into a hydrogen containing gas. The chamber is placed in communication with a nutrient containing region of a plant, and the bacterium converts the plant nutrients into the hydrogen containing gas. A device capable of utilizing hydrogen to produce electrical energy is also provided. The hydrogen utilization device is placed into communication with the gas producing device. The hydrogen containing gas flows from the chamber into the hydrogen utilization device. This device produces the usable electricity from the hydrogen content of the gas.

BRIEF DESCRIPTION OF THE DRAWINGS

To understand the present invention, it will now be described by way of example, with reference to the accompanying drawings in which.

DETAILED DESCRIPTION

Figure 1:
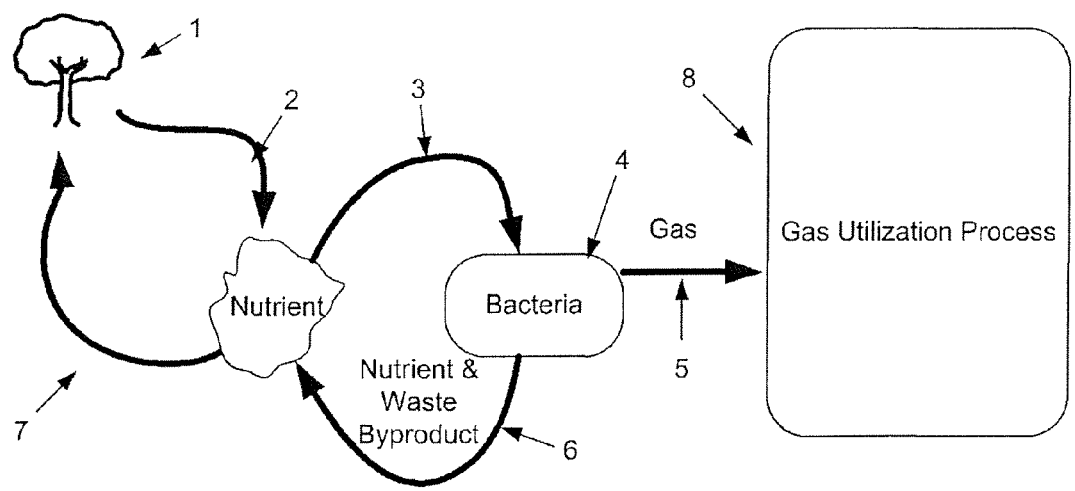
FIG. 1 is a schematic diagram illustrating one embodiment of a process for generating electrical power using plant nutrients.

While this invention is susceptible of embodiments in many different forms, exemplary embodiments of the invention are shown in the drawings and will herein be described in detail with the understanding that the present disclosure is to be considered as an exemplification of the principles of the invention and is not intended to limit the broad aspect of the invention to the embodiments illustrated.

FIG. 1 illustrates one exemplary embodiment of a process for the production of a gas from nutrients present in living plants. A plant 1 utilizes solar energy and constituents from the environment including water and carbon dioxide to produce nutrients. These nutrients 2 are extracted into a device where they are contacted 3 with bacteria 4 that are immobilized or contained by membranes. The bacteria produce a gas 5 and a small amount of liquid waste compounds. The unused nutrients with the liquid by-products 6 are returned 7 to the plant. The gas 5 is extracted and utilized to produce energy 8.

Figure 2:
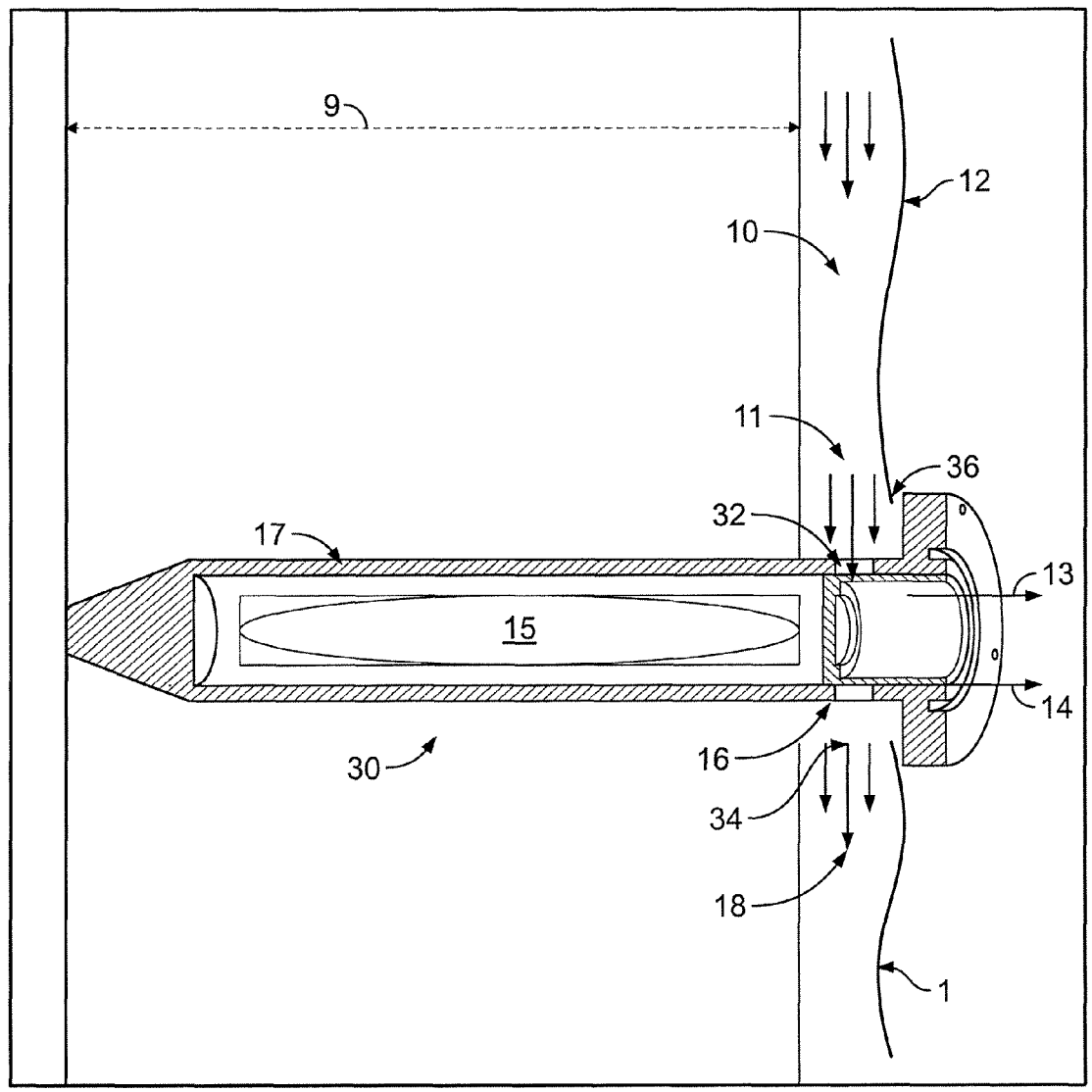
FIG. 2 is a cross-sectional view of one embodiment of a device for producing hydrogen inserted into a tree.

FIG. 2 illustrates one exemplary embodiment of a device 17 that is able to produce a hydrogen containing gas, which can be utilized to supply an integrated fuel cell. The device 17 illustrated in FIG. 2 includes a cylindrical, hollow housing 30 that can be placed inside a host plant, such as a tree 1, in such a way as to allow sap from the phloem layer 10 to flow through the device 17. The cylindrical shape allows for the utilization of a rotational drill for locating the device 17 inside the plant 1. In other embodiments, other possible placement methods inside the plant are possible and are not limited to the cylindrical shape. In further embodiments, the cross sectional area and depth of the device are sized in relation to the size of the host. Some species of plants may not be applicable to internal device hosting due to size limitations. In such cases, the device can be attached to the outside of the plant forming an airtight seal to the plant's nutrient carrying layers and allows the extraction, utilization, and redistribution of nutrients. Preferably, the device 17 is sized sufficiently small not to substantially interrupt a flow of nutrients in the plant and not to substantially reduce the structural stability of the plant. Suitable materials for construction of the device include, for example, plastic or a corrosion resistant metal, or other suitable material.

The cylindrical shape of the housing 30 illustrated in FIG. 2 also allows the housing to act as a sealing point of the device 17 to the plant 1. The cylindrical housing 30 has side openings 32, 34 that align with the phloem layer 10 when the device 17 is inserted into the plant 1. The device 17 forms an air-tight seal with the plant, so that air cannot pass from the outside into the plant 1, which is beneficial in preventing rejection mechanisms in the plant 1. Plant rejection prevention aids can be used in conjunction with placement of the device 17, such as complexing agents including Ethylene Diamine Tetra-acetic Acid, to prevent the rejection during device placement. In other embodiments, the housing 30 may have a different shape that permits such sealing. In one example, the shape could be a threaded, screw-shaped cylinder that can be inserted in a plant. In another embodiment, the vessel can have the shape of a disc that is attached to an opening in the plant exposing the phloem layer. In further embodiments, the device may be held in place by glue or a gasket that also provides sealing of the interface between the device and the plant.

In the embodiment shown in FIG. 2, the device 17 is inserted into a tree 1 through a pre-drilled hole. The device 17 is located inside the trunk 9 of the tree with the end of the device 17 extending outside the bark 12. Generally, the device 17 contains a bacterium confinement section 15 to confine, isolate, and/or immobilize the bacteria via a filter or other immobilization means, wherein the bacteria are incapable of migrating out of the chamber 15. In the embodiment illustrated in FIG. 2, the bacteria confinement chamber 15 is terminated by a porous membrane 16 that prevents the bacteria from exiting the chamber 15 and entering the sap nutrients. In other embodiments, the bacteria can be immobilized or confined inside hollow porous tubes inside the container 15. An approximately 2 μm filter material can be used for the membrane 16. The membrane 16 confines the bacteria within the confinement chamber 15, but allows gases produced by the bacteria to pass therethrough. The bacteria confined within the chamber 15 are of a type that is able to digest or otherwise process the nutrients from the plant 1 and produce a gas for use in power generation, such as hydrogen gas.

Generally, the device 17 is placed in communication with a nutrient containing region of the plant 1, such as the phloem layer 10, in order to supply the bacteria with nutrients. In the embodiment illustrated in FIG. 2, the device 17 contains a nutrient flow pathway 36, in which nutrients from the phloem layer 10 are able to flow unimpeded and reach the bacteria throughout the volume. More specifically, the nutrients 11 flowing through the phloem layer 10 enter the device 17 through the entrance openings 32, which align with the phloem layer 10. The nutrient flow passage 36 also permits the depleted nutrients and other materials 18 to flow out of the device 17 and back to the phloem layer 10. In the embodiment illustrated in FIG. 2, the exit openings 34 allow the depleted nutrients 18 to exit and return to the phloem layer 10. The nutrient passage through the wall of the device 17 is continuous to minimize pressure buildup within the host and to mitigate the possible rejection of the device 17. Further, the consistent passage of the nutrients through the device produces a convective transport into the chamber 15 and facilitates nutrient exposure to the isolated bacterium. Within the device, the nutrients are able to contact the bacteria, which convert the nutrients into a gas for use in power generation. In one exemplary embodiment, the bacteria produce hydrogen and carbon dioxide along with small concentrations of waste byproducts. These byproducts are removed from the device 17 through the exit openings 34, via the same convective stream that carries excess nutrients back into the plant.

Figure 3:
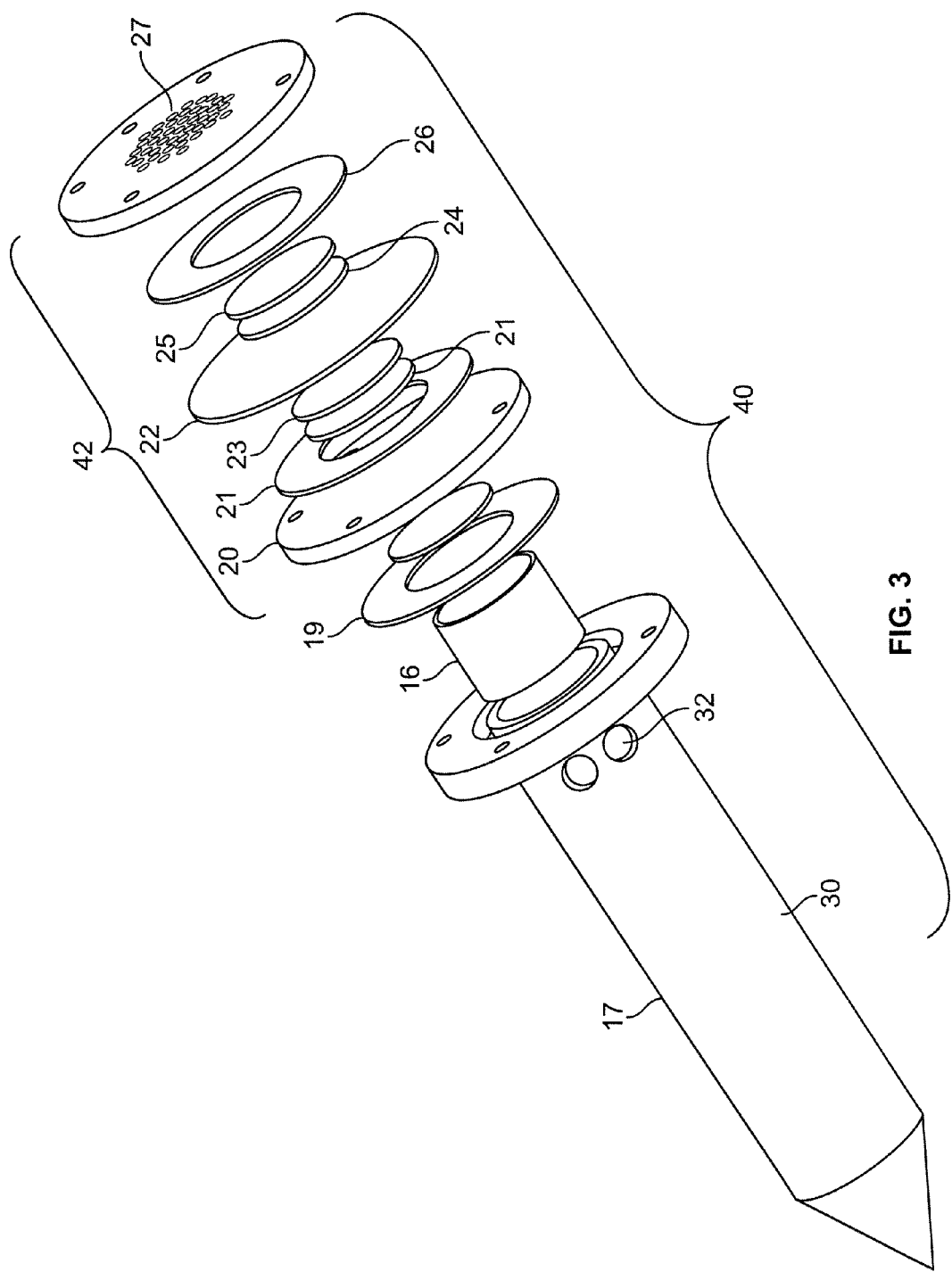
FIG. 3 is an exploded view of the device of FIG. 2 having a fuel cell connected thereto.

Generally, a gas containing hydrogen is produced by the bacteria. As illustrated in FIG. 2, the gas produced contains mostly hydrogen 13 and carbon dioxide 14, which pass through the membrane 16 and exit the device 17. In one exemplary embodiment, the gas contains more than 40 vol. % hydrogen. The hydrogen-containing gas may be used together with ambient air to produce electricity in a fuel cell. FIG. 3 illustrates one embodiment of a power generating device 40 that includes a bacteria-containing gas production device or section 17 coupled to a fuel cell section 21-29 or 42 that utilizes the gas to produce electrical energy. The gas is collected and accumulated at the top of the device 17 due to liquid/gas density difference and transported via natural diffusion through a gas/liquid separation membrane 20. This isolation membrane 20 ensures that nutrients do not exit the flow chamber within the device and do not come in contact with any section of the device that utilizes or stores the gas produced (e.g., the fuel cell 42). Suitable gas/liquid separation materials 20 are produced, for example, under the trade names Liqui-Cel® and Celgard®, though other suitable materials exist.

In the embodiment shown in FIG. 3, a hydrogen utilization device 42 is attached to the end of the bacteria-containing device 17 adjacent to the gas/liquid separation membrane 20 to form the power generating device 40. In the example illustrated, the hydrogen utilization device 42 is a Proton Exchange Membrane (PEM) fuel cell in which the hydrogen component of the product gas is utilized to produce power. Such fuel cells are known in the art, and contain flow provisions that channel the gas across the anode side of the Membrane Electrode Assembly (MEA) to effectively utilize the hydrogen component of the gas mixture. In other embodiments, hydrogen utilization devices may include hydrogen combustion engines or other external devices that require a hydrogen supply. The hydrogen can be oxidized using ambient air, producing water and electrical or mechanical energy.

FIG. 3 illustrates the fuel cell 42 attached to the bacteria-containing device 17. As illustrated, the fuel cell 42 contains seals 19, 22, 28, the gas/liquid separation membrane 20, a mechanical support and contact disc 21, gas diffusion media 24, 26, current and gas distribution layers 23, 27, and a proton-conducting catalyzed sheet (PEM sheet) 25. The fuel cell 42 is terminated with a perforated disc 29. The contact disc 21 on the anode side of the fuel cell contains flow provisions to channel the gas mixture through the gas diffusion and distribution media to utilize a maximum amount of the hydrogen content. The anode gas mixture is exhausted through a positive pressure sealing section in gasket 22.

Suitable gas diffusion media 24, 26 are commercially available, for example, from E-Tek, Inc. or Ballard Power Systems, Inc. The adjacent layers 23, 27 can be made from the same material. In other embodiments, the layers 23, 27 may be omitted, or may be made from expanded metal foils made from corrosion resistant materials. Suitable catalyzed PEM sheets 25 can be obtained from DuPont, E-Tek, Inc., or W. L. Gore and Associates, or other commercial providers. The seals 19, 22, 28 can be manufactured, for example, from flexible plastic by stamping or similar techniques. The discs 21, 29 can be manufactured, for example, by machining from conductive corrosion resistant materials such as metals or graphite containing composites.

The power generating device 40 can be implanted or attached to living plants. The device 40 can power electronic devices that include, but are not limited to, wireless and wired sensors, communication equipment, remote actuators, data acquisition devices, cameras, and energy storage devices. In one exemplary embodiment, the device 17 forms a power supply for remote wireless sensors and uses tree or cactus nutrients as energy source.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying claims.

What is claimed is:

1. A method for producing usable electricity for an extended period of time, comprising:
    providing a gas producing device containing a bacterium which is confined within a chamber capable of converting plant nutrients into a hydrogen containing gas;
    placing the gas producing device in communication with a nutrient containing region of a plant which forms an air-tight seal with the plant, wherein the bacterium converts the plant nutrients into the hydrogen containing gas;
    providing a hydrogen utilization device capable of utilizing hydrogen to produce electrical energy; and
    placing the hydrogen utilization device into communication with the gas producing device, wherein the hydrogen containing gas flows from the gas producing device chamber containing a porous membrane that allows gases passage into the hydrogen utilization device, and the hydrogen utilization device produces the usable electricity from hydrogen in the hydrogen containing gas.

2. The method of claim 1, wherein the hydrogen utilizing device comprises an integrated fuel cell energy conversion device.

3. The method of claim 1, wherein the hydrogen utilizing device comprises an integrated combustion engine energy conversion device.

4. The method of claim 1, further comprising inserting the gas producing device into the plant, in contact with the nutrient containing region.

5. The method of claim 1, further comprising passing spent nutrient liquid back into the plant after contact with the bacterium.

* * * * *